US00PP20912P2

(12) United States Plant Patent
de Jong

(10) Patent No.: US PP20,912 P2
(45) Date of Patent: Mar. 30, 2010

(54) ***SYMPHORICARPOS* PLANT NAMED 'KOLMGALA'**

(50) Latin Name: *Symphoricarpos alba*
Varietal Denomination: Kolmgala

(75) Inventor: Jan de Jong, Heelsum (NL)

(73) Assignee: Kolster Beheer B.V., Boskoop (NL)

( * ) Notice: Subject to any disclaimer, the term of this patent is extended or adjusted under 35 U.S.C. 154(b) by 0 days.

(21) Appl. No.: 12/315,316

(22) Filed: Dec. 2, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—June Hwu
(74) *Attorney, Agent, or Firm*—C. A. Whealy

(57) ABSTRACT

A new and distinct cultivar of *Symphoricarpos* plant named 'Kolmgala', characterized by its compact, upright and outwardly spreading plant habit; short stems and internodes, bushy and dense habit; freely flowering habit; numerous white-colored berries; and good garden performance.

3 Drawing Sheets

Botanical designation: *Symphoricarpos alba.*
Cultivar denomination: 'Kolmgala'.

BACKGROUND OF THE INVENTION

The present invention relates to a new and distinct cultivar of *Symphoricarpos* plant, botanically known as *Symphoricarpos alba* and hereinafter referred to by the name 'Kolmgala'.

The new *Symphoricarpos* plant is a product of a planned breeding program conducted by the Inventor in Heelsum, The Netherlands. The objective of the breeding program is to create new pot-type *Symphoricarpos* cultivars with strong foliage and numerous attractive fruits.

The new *Symphoricarpos* plant originated from a cross-pollination in 2001 in Heelsum, The Netherlands of a proprietary selection of *Symphoricarpos alba* identified as code number 99-22, not patented, as the female, or seed parent with a proprietary selection of *Symphoricarpos alba* identified as code number 01-02, not patented, as the male, or pollen, parent. The new *Symphoricarpos* was discovered and selected by the Inventor as a single flowering plant within the progeny of the stated cross-pollination in a controlled greenhouse environment in Heelsum, The Netherlands in 2003.

Asexual reproduction of the new *Symphoricarpos* plant by vegetative cuttings in Boskoop, The Netherlands since 2003 has shown that the unique features of this new *Symphoricarpos* plant are stable and reproduced true to type in successive generations.

SUMMARY OF THE INVENTION

Plants of the new *Symphoricarpos* have not been observed under all possible environmental conditions. The phenotype may vary somewhat with variations in environment such as temperature and light intensity without, however, any variance in genotype.

The following traits have been repeatedly observed and are determined to be the unique characteristics of 'Kolmgala'. These characteristics in combination distinguish 'Kolmgala' as a new and distinct cultivar of *Symphoricarpos:*

1. Compact, upright and outwardly spreading plant habit.
2. Short stems and internodes, bushy and dense habit.
3. Freely flowering habit.
4. Numerous white-colored berries.
5. Good garden performance.

Plants of the new *Symphoricarpos* differ primarily from plants of the female parent selection in the following characteristics:

1. Plants of the new *Symphoricarpos* have shorter lateral branches than plants of the female parent selection.
2. Plants of the new *Symphoricarpos* have darker green-colored leaves than plants of the female parent selection.

Plants of the new *Symphoricarpos* differ primarily from plants of the male parent selection in the following characteristics:

1. Plants of the new *Symphoricarpos* have shorter lateral branches than plants of the male parent selection.
2. Plants of the new *Symphoricarpos* are more freely flowering and fruiting than plants of the male parent selection.
3. Plants of the new *Symphoricarpos* have smaller fruits than plants of the male parent selection.

Plants of the new *Symphoricarpos* can be compared to plants of *Symphoricarpos* 'Magical White', not patented. Plants of the new *Symphoricarpos* differ primarily from plants of 'Magical White' in plant habit as plants of the new *Symphoricarpos* are more compact and denser than plants of 'Magical White'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Symphoricarpos.*

The photograph on the first sheet comprises a side perspective view of a typical plant of 'Kolmgala' grown in a container.

The photograph at the top of the second sheet is a close-up view of typical developing and open flowers of 'Kolmgala';

the photograph at the bottom of the second sheet is a close-up view of a typical leaf and stem of 'Kolmgala'.

The photograph on the third sheet is a close-up view of typical fruits of 'Kolmgala'.

DETAILED BOTANICAL DESCRIPTION

Plants used for the aforementioned photographs and following description were grown for two years under conditions which closely approximate commercial *Symphoricarpos* production conditions in containers in an outdoor nursery in Boskoop, The Netherlands during the summer. During the production of the plants, day temperatures ranged from 7° C. to 30° C. and night temperatures ranged from 3° C. to 16° C. In the following description, color references are made to The Royal Horticultural Society Colour Chart, 2001 Edition, except where general terms of ordinary dictionary significance are used.

Botanical classification: *Symphoricarpos alba* 'Kolmgala'.

Parentage:

*Female, or seed, parent.*—Proprietary selection of *Symphoricarpos alba* identified as code number 99-22, not patented.

*Male, or pollen, parent.*—Proprietary selection of *Symphoricarpos alba* identified as code number 01-02, not patented.

Propagation:

*Type cutting.*—Vegetative cuttings.

*Time to initiate roots.*—About five weeks at 18° C. to 25° C.

*Time to produce a rooted young plant.*—About eight weeks at 18° C. to 25° C.

*Root description.*—Medium in thickness; fibrous; creamy white in color.

*Rooting habit.*—Moderately freely branching; sparse.

Plant description:

*Form/growth habit.*—Perennial shrub. Compact, upright and outwardly spreading plant habit; broadly inverted triangle; short stems and internodes, bushy and dense habit; moderately vigorous growth habit.

*Branching habit.*—Freely basally branching habit with about 44 lateral branches.

*Plant height.*—About 48.5 cm.

*Plant width* (*spread*).—About 47.2 cm.

*Lateral branch description.*—Length: About 32.6 cm. Diameter: About 2 mm. Internode length: About 3.2 cm. Strength: Strong. Texture: Smooth, glabrous. Color, developing: Close to 182B to 182C. Color, developed: Close to 199C to 199D.

Foliage description:

*Arrangement.*—Opposite, simple.

*Length.*—About 3.4 cm.

*Width.*—About 2.5 cm.

*Shape.*—Ovate.

*Apex.*—Broadly acute to acuminate.

*Base.*—Attenuate.

*Margin.*—Entire, undulate.

*Texture, upper and lower surfaces.*—Smooth, glabrous; slightly rugose.

*Venation pattern.*—Pinnate.

*Color.*—Developing leaves, upper surface: Close to 143A. Developing leaves, lower surface: Close to 138B. Fully expanded leaves, upper surface: Close to 137A; venation, close to 144B to 144C. Fully expanded leaves, lower surface: Close to 138A to 138B; venation, close to 144C to 144D.

*Petioles.*—Length: About 5 mm. Diameter: About 1 mm. Texture, upper and lower surfaces: Smooth, glabrous. Color, upper and lower surfaces: Close to 146C to 146D.

Flower description:

*Flower arrangement and shape.*—Single campanulate flowers arranged in terminal spikes or solitary in leaf axils; freely flowering habit with about 16 flowers per spike. Flowers face outwardly to drooping.

*Fragrance.*—None detected.

*Natural flowering season.*—From July to September in The Netherlands.

*Flower longevity.*—Flowers last about five days on the plant; flowers not persistent.

*Fruit longevity.*—About one month.

*Flower buds.*—Length: About 6 mm. Diameter: About 3 mm. Shape: Orbicular. Color: Close to 185B to 185D.

*Inflorescence size.*—Height: About 2 cm. Diameter: About 1.4 cm.

*Flowers.*—Diameter: About 5 mm. Depth (height): About 8 mm.

*Petals.*—Quantity/arrangement: Five in a single whorl; petals fused towards the base. Length: About 5.5 mm. Width: About 3 mm. Shape: Elliptic. Apex: Broadly acute. Margin: Entire. Texture, upper surface: Pubescent. Texture, lower surface: Glabrous, smooth. Color: When opening, upper and lower surfaces: Close to 186D; towards the apex, close to N155A. Fully opened, upper surface: Close to 186D. Fully opened, lower surface: Close to 186B.

*Sepals.*—Quantity/arrangement: Five in a single whorl; sepals fused below the apices; calyx, funnelform. Length: About 3 mm. Width: About 1 mm. Apex: Acute. Margin: Entire. Texture, upper and lower surfaces: Glabrous, smooth. Color: When opening and fully opened, upper surface: Close to 148A. When opening and fully opened, lower surface: Close to 143C; at the apex, close to 183C.

*Peduncles.*—Strength: Moderately strong. Length: About 1.7 cm. Diameter: About 1 mm. Texture: Smooth, glabrous. Color: Close to 178A to 178B.

*Pedicels.*—Strength: Moderately strong. Length: About 1 mm. Diameter: About 0.8 mm. Texture: Smooth, glabrous. Color: Close to 144B to 144C.

*Reproductive organs.*—Stamens: Quantity per flower: About five. Filament length: About 1.5 mm. Filament color: Close to N155A. Anther shape: Narrowly oblong. Anther length: About 1 mm. Anther color: Close to 4C to 4D. Pollen amount: Scarce. Pollen color: Close to 4C. Pistils: Quantity per flower: One. Pistil length: About 4 mm. Stigma shape: Club-shaped. Stigma color: Close to 144D. Style length: About 3.5 mm. Style color: Close to 157D. Ovary color: Close to 143B.

*Fruits.*—Length: About 1.2 cm Diameter: About 1.4 cm. Shape: Roughly spherical. Texture: Smooth, glabrous. Color: Close to 155C.

*Seeds.*—Length: About 3 mm. Diameter: About 2 mm. Color: Close to 158B.

Disease/pest resistance: Plants of the new *Symphoricarpos* have been noted to be resistant to *Puccinia* rust. Plants of the new *Symphoricarpos* have not been observed to be resistant to pests and other pathogens common to *Symphoricarpos.*

Weather/temperature tolerance: Plants of the new *Symphoricarpos* have been observed to tolerate wind, rain and temperatures ranging from about −25° C. to about 40° C.

It is claimed:

1. A new and distinct *Symphoricarpos* plant named 'Kolmgala' as illustrated and described.

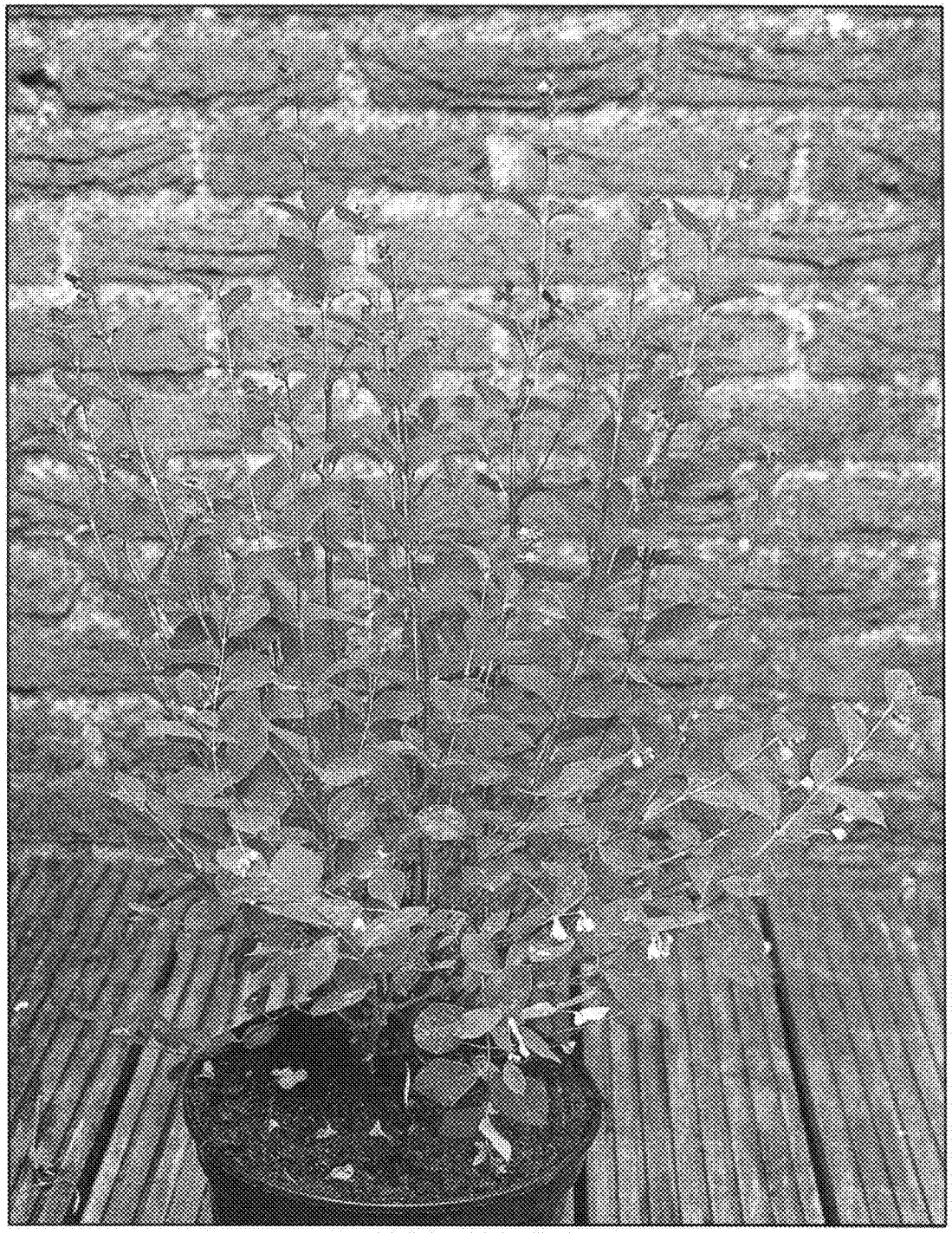

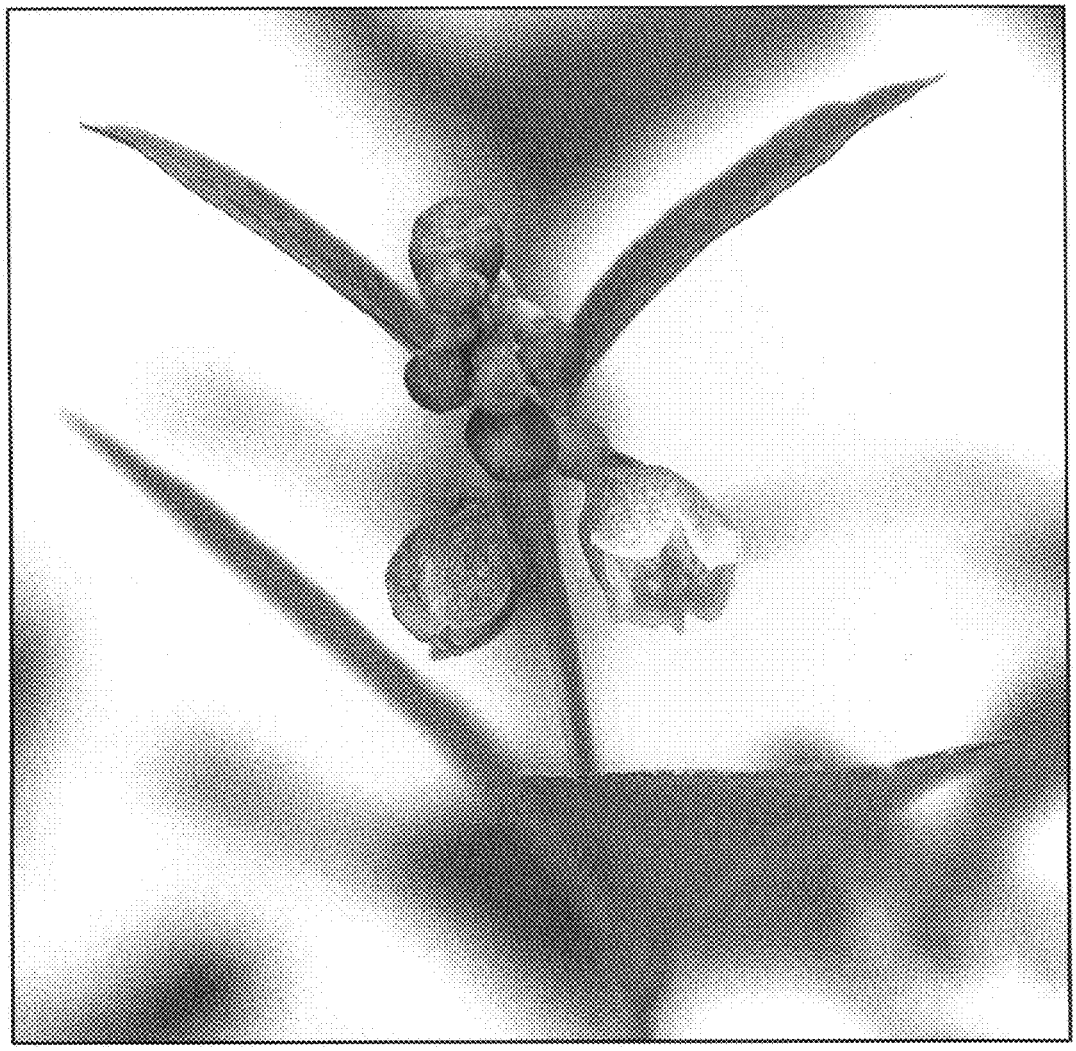
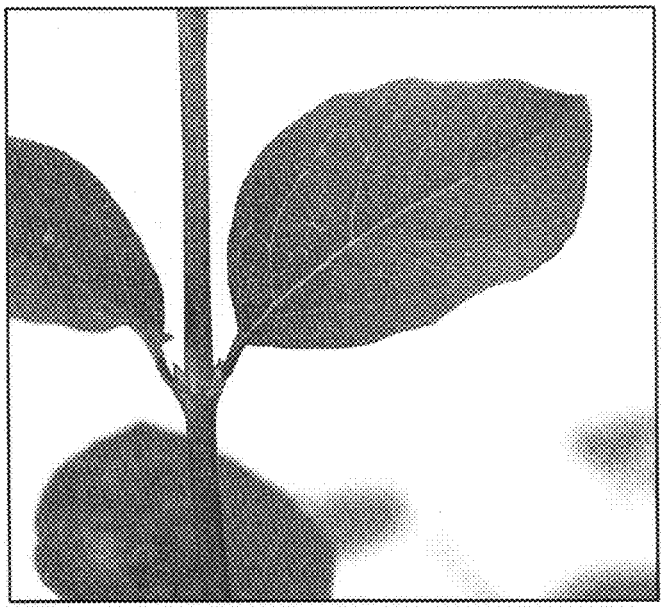

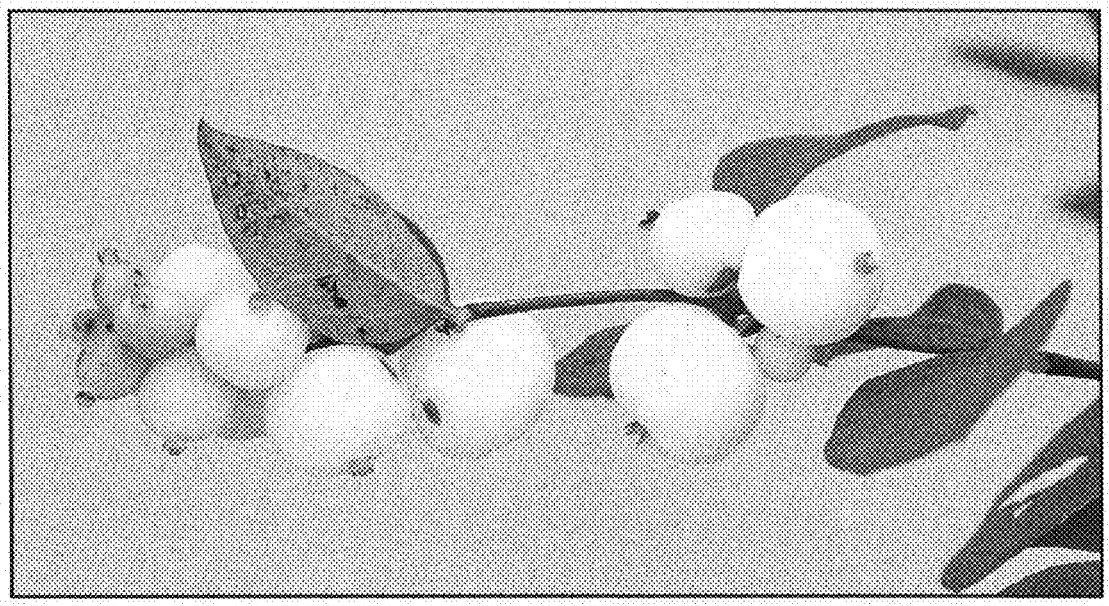

* * * * *